(12) United States Patent
Stierstorfer

(10) Patent No.: US 8,873,704 B2
(45) Date of Patent: Oct. 28, 2014

(54) FILTER FOR AN X-RAY DEVICE, AND X-RAY DEVICE EMBODYING SUCH A FILTER

(75) Inventor: Karl Stierstorfer, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 324 days.

(21) Appl. No.: 13/369,630

(22) Filed: Feb. 9, 2012

(65) Prior Publication Data

US 2012/0219106 A1    Aug. 30, 2012

(30) Foreign Application Priority Data

Feb. 25, 2011   (DE) .......................... 10 2011 004 742

(51) Int. Cl.
*G21K 1/12*     (2006.01)
*A61B 6/00*     (2006.01)
*A61B 6/03*     (2006.01)
*G21K 1/10*     (2006.01)

(52) U.S. Cl.
CPC ............... *A61B 6/032* (2013.01); *A61B 6/4035* (2013.01); *G21K 1/10* (2013.01)
USPC .............................. 378/16; 378/158; 378/159

(58) Field of Classification Search
CPC .......... A61B 6/035; A61B 6/542; A61B 6/06; A61B 6/4035; G21K 1/02; G21K 1/04; G21K 1/046; G21K 1/10
USPC ..................................... 378/16, 145, 156–159
See application file for complete search history.

(56) References Cited

U.S. PATENT DOCUMENTS

| | | |
|---|---|---|
| 7,088,799 B2 | 8/2006 | Hoffman |
| 7,330,535 B2 | 2/2008 | Arenson et al. |
| 7,680,249 B2 * | 3/2010 | Yuan .............................. 378/158 |
| 7,688,935 B2 | 3/2010 | Toth |

FOREIGN PATENT DOCUMENTS

| | | |
|---|---|---|
| JP | 2006271437 A | 10/2006 |
| JP | 2007268241 A | 10/2007 |

* cited by examiner

*Primary Examiner* — Jurie Yun
(74) *Attorney, Agent, or Firm* — Schiff Hardin LLP

(57) ABSTRACT

A filter for an x-ray device to shape an intensity profile of x-ray radiation emanating from an x-ray source of the device has a filter body made of a material that attenuates x-ray radiation. The filter body is designed with a propeller shape and has two blades connected by an axle of the filter. The filter body is rotatable around the axle, which is permeable to the x-ray radiation. The x-ray device embodies at least one such filter.

9 Claims, 3 Drawing Sheets

FILTER FOR AN X-RAY DEVICE, AND X-RAY DEVICE EMBODYING SUCH A FILTER

BACKGROUND OF THE INVENTION

1. Field of the Invention

The present invention concerns a filter for an x-ray device to shape an intensity profile of x-ray radiation emanating from an x-ray source of the x-ray device. The invention also concerns an x-ray device that has at least one such filter.

2. Description of the Prior Art

In the acquisition of x-ray projections of a body region of a patient (in particular for diagnostic purposes), it is common practice to use shaping filters. Such a shaping filter is typically associated with an x-ray source in order to at least partially shade, attenuate or at least partially absorb the x-ray radiation emanating from the x-ray source. Such a shaping filter is normally designed such that specific peripheral body regions of a patient (such as the arm) that, due to their smaller thickness, have a lower radiation attenuation for x-ray radiation, are at least partially shaded given a central projection, for example. This means that the x-rays emanating from the x-ray source first penetrate the shaping filter and only then penetrate the shaded body region of the patient with lower intensity. Conversely, central regions are not shaded by the shaping filter.

Such an embodiment of a shaping filter has the advantage that specific body regions of the patient (such as the noted arms) are not exposed to an unnecessarily high intensity of x-ray radiation for the imaging. If the complete scan of a patient is considered, the dose of x-ray radiation applied to the patient can also be reduced in this way. Furthermore, the shaping filter produces a certain homogenization of the x-ray radiation passing through the patient and received by an x-ray detector, meaning that the shaping filter at least partially compensates the inherently inhomogeneous signal curve so that the noise in the x-ray detector also varies less from location to location, which is desirable.

Such, a shaping filter is normally designed for a defined, average patient geometry or a beam attenuation profile of an average patient, such that the effects of the dose savings and the homogenization lead to results of different quality in different patients. An additional disadvantage occurs in the case of static shaping filters in x-ray devices such as computed tomography apparatuses in which the shaping filter rotates with the x-ray source around a patient. Depending on the rotation angle or projection angle for the acquisition of x-ray projections, the patient geometry and the beam attenuation profile of the patient thereby will be different; so a static shaping filter cannot be adapted to such a dynamic situation.

In U.S. Pat. No. 7,088,799 B2 a filter for an x-ray device is described that is designed with a cylindrical shape, and has multiple filter profiles and is rotatable around the longitudinal axis of the cylinder.

From U.S. Pat. No. 7,330,535 B2 a filter arrangement for an x-ray device is known that has a pair of bow tie filters. The filters are executed in a u-shape and are pivotable around an axis.

In U.S. Pat. No. 7,688,936 B2 a filter arrangement is described that has a set of filters that are arranged on a hub that is rotatable around an axis. The individual filters in the set of filters differ from one another and are used with different tube voltages applied to an x-ray tube of a CT apparatus for a multiple-energy data acquisition.

SUMMARY OF THE INVENTION

An object of the present invention is to provide a filter for an x-ray device, and an x-ray device of the aforementioned type, such that the intensity profile of x-ray radiation emanating from an x-ray source can be shaped specifically to the examination subject, at least in part.

According to the invention, this object is achieved by a filter for an x-ray device to shape an intensity profile of x-ray radiation emanating from an x-ray source of the device, and the filter has a filter body formed in a propeller shape with two blades connected by an axle of the filter that are each made of a material attenuating x-ray radiation. The filter body is rotatable around the axle (which is permeable to the x-ray radiation). Because the filter body is rotatable around the axle, the filter body can change its x-ray attenuation profile by virtue of the blades having a design that is appropriate for the x-ray source with which it is associated. In particular, the intensity profile of the x-ray radiation emanating from the associated x-ray source (the intensity profile being shaped or produced by the filter or by the filter body) can be altered or varied.

In an embodiment of the invention, the filter body of the filter is designed such that, given arrangement of the filter in the beam path of the x-ray radiation emanating from the x-ray source and given rotation of the filter body around the axle of the filter, the radiography lengths can be changed or varied by the filter body for at least a portion of the x-rays of the x-ray radiation.

According to another embodiment of the invention, the filter body can be aligned by pivoting or rotating around the axle such that the intensity profile of the x-ray radiation, that is shaped by the filter or filter body, can be adapted to the geometric dimensions and/or the beam attenuation profile of a subject to be exposed with the x-ray radiation.

According to a further embodiment of the invention, by intermittent or continuous pivoting or rotation of the filter body around the axle, the intensity profile of the x-ray radiation that is shaped by the filter or the filter body can be adapted intermittently or continuously to the varying geometric dimensions and/or to a varying beam attenuation profile of a subject to be exposed with the x-ray radiation, as "seen" by the x-ray radiation.

In an embodiment of the invention, the one blade of the propeller-shaped filter body is designed to be approximately wave-shaped in cross section (i.e., a cross-section approximating a wave crest of a fluid wave), and the other blade is designed to be approximately banana-shaped in cross section. The axle of the filter or filter body preceding between the two blades defines a longitudinal direction. The filter body normally does not vary in shape in the longitudinal direction.

In an embodiment of the invention that the filter body has aluminum and/or graphite as the filter material.

The above object of the invention is also achieved by an x-ray device that has at least one filter as described above.

In an embodiment of the inventive device, the x-ray device has at least one x-ray source that emits a pyramid-shaped, conical or fan-shaped beam of x-rays, the pyramid-shaped, conical or fan-shaped beam of x-rays having an axis of symmetry, and the filter is mechanically or geometrically associated with the x-ray source such that, due to the filter body, the radiography lengths of the x-rays of the beam of x-rays are always approximately symmetrical to the axis of symmetry, even given a pivoted filter body. The filter body is thereby designed such that, by pivoting the filter body around the axle of the filter or of the filter body, the radiography lengths in the two border regions of the filter body can be increased in comparison to the central region of the filter body or more significantly increased.

In a further embodiment of the invention, the x-ray device is a computed tomography apparatus with at least one x-ray source and one x-ray detector that are arranged opposite one another on a portion of a gantry of the computed tomography apparatus that is rotatable around a system axis, and the filter that shapes the intensity profile is associated with the at least one x-ray source.

According to a further embodiment of the invention, the filter body can be pivoted around the axle synchronously with the rotation of the rotatable part of the gantry around the system axis, such that the intensity profile of the x-ray radiation emanating from the at least one x-ray source, or the beam attenuation profile of the filter body, is always adapted to the projection angle-dependent beam attenuation profile of a subject to be examined, during operation of the computed tomography apparatus.

According to an embodiment of the invention, the filter body performs a see-saw motion. The filter body thus does not rotate through 360°, but rather swings (oscillates back and forth) between +/−x°, wherein the angle x depends on the shape of the filter body.

DESCRIPTION OF THE PREFERRED EMBODIMENTS

Figure 1:
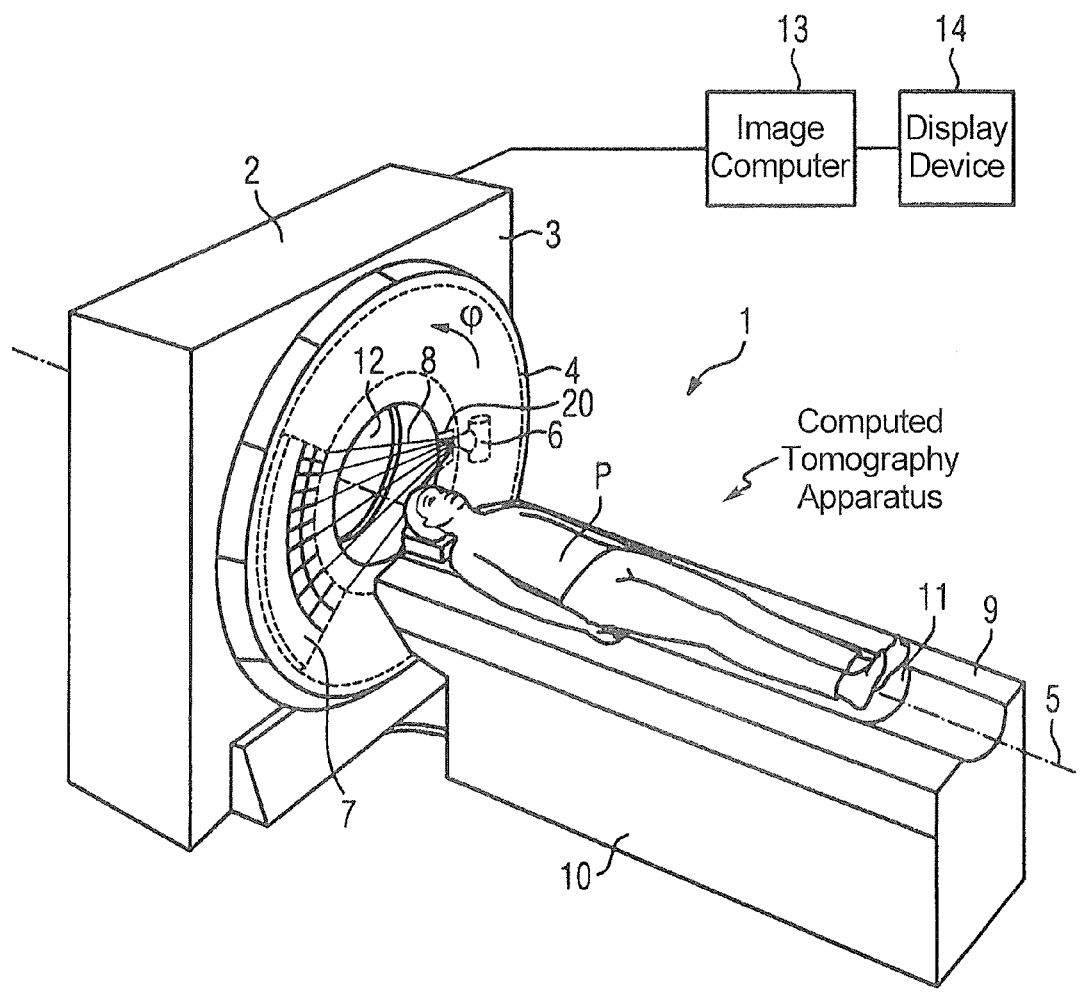
FIG. 1 schematically illustrates a computed tomography apparatus with a filter according to the invention

Identical or functionally identical elements are provided with the same reference characters throughout Figures. The representations in Figures are schematic and not necessarily true to scale. The computed tomography apparatus 1 is discussed in the following and without limitation of the generality only insofar as it is deemed necessary to understand the invention.

The computed tomography apparatus 1 shown in FIG. 1 has a gantry 2 with a stationary part 3 and with a part 4 that is rotatable around a system axis 5. In the exemplary embodiment of the invention, the rotatable part 4 has an x-ray system that includes an x-ray source 6 and an x-ray detector 7 that are arranged opposite one another on the rotatable part 4. During operation of the computed tomography apparatus 1, x-ray radiation 8 in the form of a fan-shaped beam 8 of x-rays emanates from the x-ray source 6 in the direction of the x-ray detector 7, penetrates a measurement subject and is detected by the x-ray detector 7 in the form of measurement data or measurement signals.

Furthermore, the computed tomography apparatus 1 has a patient bed 9 to support a patient P to be examined. The patient bed 9 has a bed base 10 on which is arranged a patient support plate 11 provided to actually bear the patient P. The patient support plate 11 is adjustable relative to the bed base 10 in the direction of the system axis 5 such that it, together with the patient P, can be introduced into the opening 12 of the gantry 2 to acquire x-ray projections of the patient P, for example in a spiral scan. The computational processing of the x-ray projections acquired with the x-ray system or, respectively, the reconstruction of slice images, 3D images or a 3D data set based on the measurement data or the measurement signals of the x-ray projections takes place with an image computer 13 of the computed tomography apparatus 1, which slice images or 3D images can be presented at a display device 14.

A filter 20 according to the invention is associated with the x-ray source 6 (which is presently an x-ray tube) in order to continuously shape the intensity profile of the x-ray radiation 8 emanating from the x-ray source 6 such that it is adapted optimally well to the projection angle-dependent beam attenuation profile of the patient P. The filter 20 is arranged before the x-ray source 6, as viewed in the direction of the x-ray radiation 8 emanating from the x-ray source 6.

Figure 2:
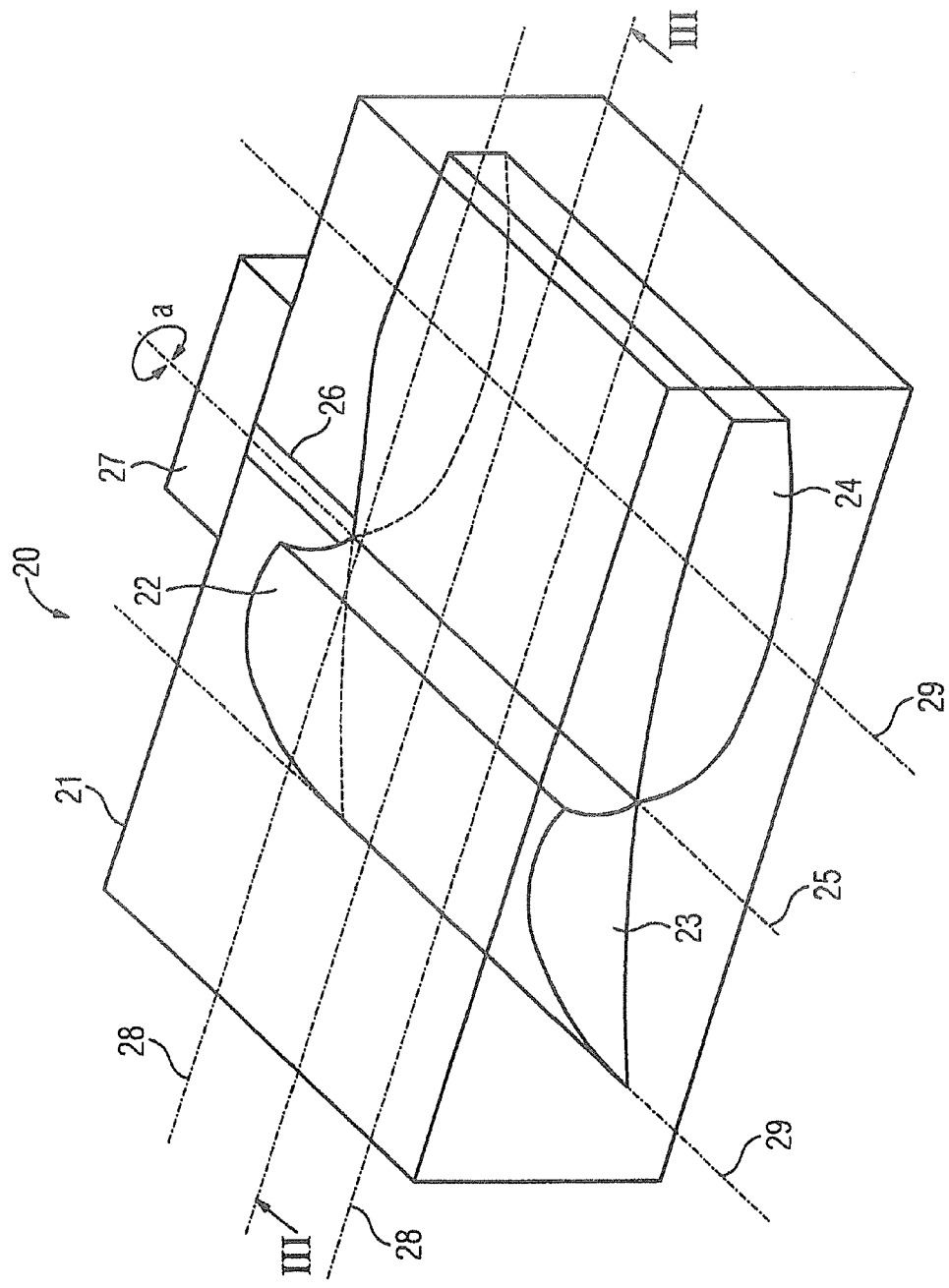
FIG. 2 shows the filter of the computed tomography apparatus from FIG. 1.

In FIG. 2, the filter 20 is shown in a perspective presentation. In the present exemplary embodiment of the invention, the filter 20 has a cuboid housing 21 permeable by x-ray radiation. The housing 21 is fashioned from a plastic, for example. Arranged in the housing 21 is a filter body 22 made of or includes a material that attenuates x-ray radiation, such as aluminum and or graphite, for example.

In the exemplary embodiment of the invention, the filter body 22 is propeller-shaped in design and has two blades 23, 24 that are connected with one another by an axle 25 of the filter 20 or of the filter body 22, around which the filter body 22 can be rotated or pivoted. In the exemplary embodiment of the invention, the filter 20 or filter body 22 has a shaft 26 capable of being driven, the shaft 26 and the axle 25 being co-linear. The shaft 26 is firmly connected with the filter body 22 so that the filter body 22 can also be specifically rotated or pivoted by rotation or pivoting of the shaft 26 in the directions of the double arrow a. In the present exemplary embodiment of the invention, the pivoting of the shaft 26 (and thus of the filter body 22) is produced by an electric drive 27.

The arrangement of the filter 20 on the rotatable part 4 of the gantry 2, as well as the association with the x-ray source 6, moreover takes place such that the shaft 26 and the drive 27 of the filter 20 are always located outside of the area of the filter 20 that is permeated by x-ray radiation, and thus are not active in the image. For example, this can be ensured with diaphragms. For illustration in this regard, in FIG. 2 diaphragms 28 are shown that establish the width of the fan-shaped beam 8 of x-rays, which are active in the Z-direction or in the direction of the system axis 5, and diaphragms 29 (schematically drawn) are shown that establish the aperture of the fan-shaped beam 8 of x-rays, which are active in the φ-direction.

To stabilize the filter body 22 in the direction of the axle 25, the filter 20 can have a plate (not shown) on its front side and/or rear side, to which plate are attached the blades 23, 24 of the filter body 22 as well as the shaft 26. In this embodiment of the filter 20, the plates and the shaft 26 are again located outside of the region of the filter 20 that is permeated by the x-ray radiation 8.

The filter body 22—in particular the two blades 23, 24 of the filter body 22—are designed such that, given arrangement of the filter 20 in the beam path of the x-ray radiation 8 emanating from the x-ray source 6, and given rotation of the filter body 22 around the axis 25, for at least a portion of the x-rays of the x-ray radiation 8 the radiography lengths change due to the filter body 22, thus the distances that the individual x-rays travel through the filter body until they exit from this again after their entrance. The radiography lengths are essentially symmetrical to the plane of symmetry S of the beam 8 of x-rays emanating from the x-ray source 6 since the majority of examination subjects have a certain symmetry (at least if they are people). The plane of symmetry S travels through the axle 25 and the focus of the x-ray source 6 and splits the fan-shaped beam 8 of x-rays into two equally large partial fans, as this is apparent from FIG. 3.

Figure 3:
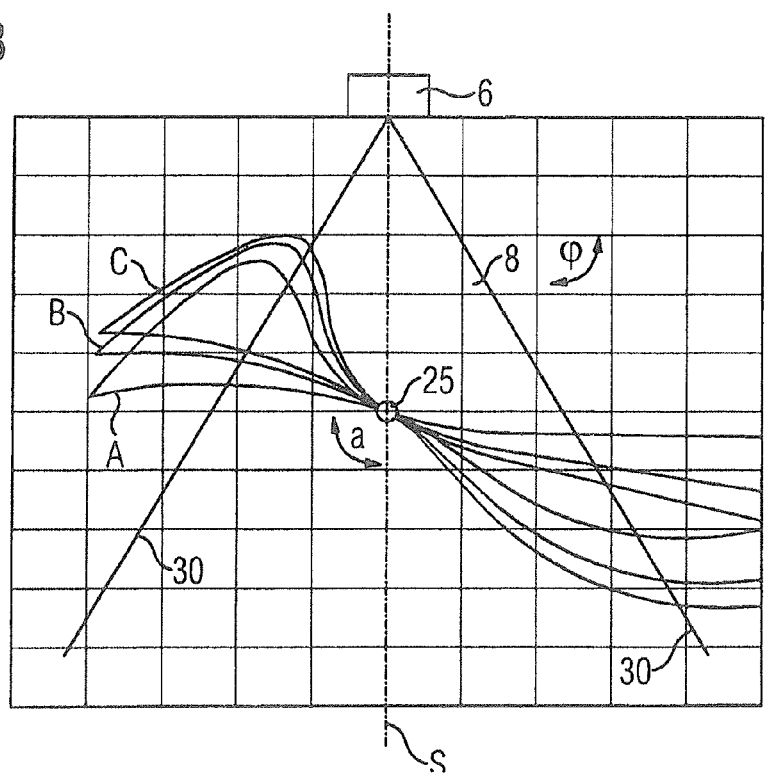
FIG. 3 is an illustration of the function of the filter from FIG. 2.
Figure 4:
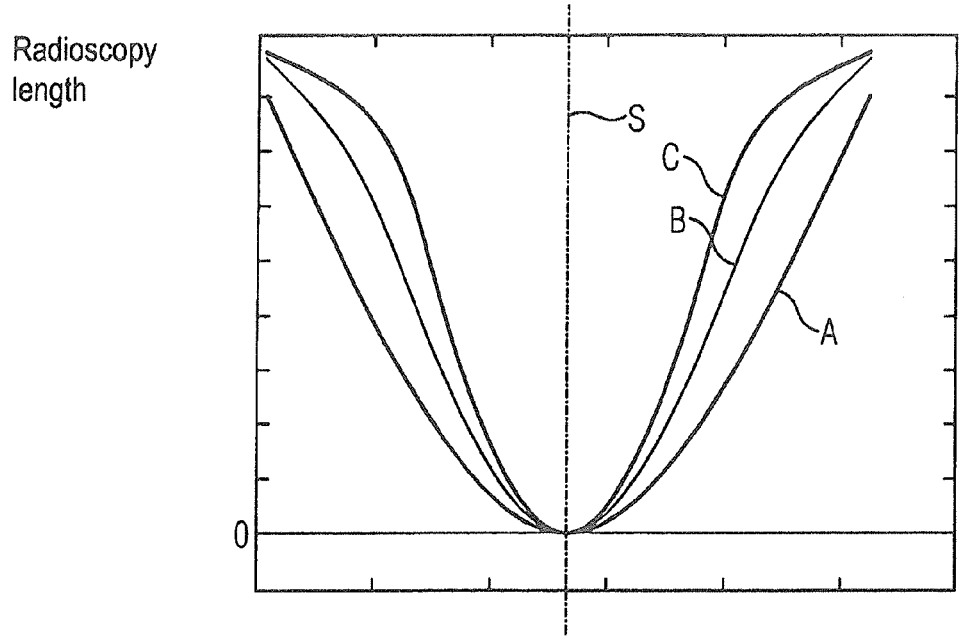
FIG. 4 is an illustration of the radiography lengths through the filter body of the filter from FIG. 2 at different pivot positions of the filter body.

In order to achieve the symmetry of the radiography lengths to the plane of symmetry S even given a pivoted filter body 22, the first blade 23 is approximately undulating in design as seen in cross section relative to the axle 25, and the second blade 24 is approximately banana-shaped in design as considered in cross section relative to the axle 25. The symmetry of the radiography lengths given a pivoted filter body 22 is illustrated in FIGS. 3 and 4 for three different pivot positions of the filter body 22 around the axle 25. The filter body 22 is shown in section for this in FIG. 3 (see FIG. 2, Section III-III). It is also to be learned from FIG. 3 that the filter body 22 itself has no symmetry with the axle 25 and the plane of symmetry S. Additionally, the edge rays 30 of the fan-shaped beam 8 of x-rays emanating from the x-ray source 6 (possibly limited by the diaphragms 29) that are established in the φ-direction are plotted in FIG. 3. In the case of the present exemplary embodiment of the invention, the axle 25 of the filter 20 travels essentially parallel to the system axis 5 of the computed tomography apparatus 1.

Using the three pivot positions A, B and C of the filter body 22, it is apparent from FIG. 3 that the radiography lengths of x-rays emanating from the x-ray source 6 through the filter body 2 are changed by rotating or pivoting the filter body 22 around the axle 25. Using three curves for the three pivot positions A, B and C of the filter body 22, FIG. 4 illustrates the radiography lengths changing symmetrically with the plane of symmetry S as viewed across the cross-section of the filter body 22. It can be seen that, due to the pivoting of the filter body, the edge steepness of the curves of the radiography lengths increases from the pivot positions A to the pivot positions C.

If the x-ray source 6 arranged at the rotatable part 4 of the gantry 2 is located in the twelve o'clock or six o'clock position, the filter body 22 assumes the pivot position A in the acquisition of an x-ray projection in the chest region of the patient P in order to adapt the intensity profile of the x-ray radiation 8 to the body geometry or, respectively, body cross section the geometry of the patient P to be exposed or, respectively, the prevailing beam attenuation profile of the patient P. In the position A, the intensity of the x-ray radiation 8 in the region of the arm of the patient P is reduced in the desired manner relative to the intensity of the x-ray radiation 8 in the central or back region of the patient P.

In contrast to this, if the x-ray source 6 is located in the three o'clock or nine o'clock position, the filter body 22 advantageously assumes the pivot position C in the acquisition of an x-ray projection into the chest region of the patient P. In this case, as viewed in the projection direction the body cross section geometry of the patient P is markedly more compressed. For this reason, the intensity profile can also be narrowed via the filter 20 or, respectively, the filter body 22. The radiography lengths of the x-rays are therefore increased at the outsides so that the border regions of the filter body 22 attenuate the x-ray radiation.

The filter body 22 thus changes its beam attenuation profile via rotation or pivoting around the axle 25. As a consequence of this, the resulting intensity profile of the x-ray radiation emanating from the x-ray source 6 changes due to rotation or pivoting of the filter body 22.

In the course of a scan of the patient P with the computed tomography apparatus 1 in which x-ray projections of the body of the patient P are acquired from different directions with feed of the patient support plate 11 (accommodating the patient P) in the direction of the system axis 5, the filter body 22 is pivoted around the axle 25 depending on the projection angle in order to respectively adapt the intensity profile of the x-ray radiation 8 emanating from the x-ray source 6 to the projection angle-dependent beam attenuation profile of the patient P. The pivoting of the filter body 22 around the axle 25 is thereby synchronized with the rotation of the rotatable part 4 of the gantry 2 around the system axis 5. For this, the drive 27 of the filter 20 is correspondingly activated by a control device (not explicitly shown) of the computed tomography apparatus 1 to which the rotation positions of the rotatable part 4 of the gantry 2 are known, for example via an incremental sensor of the gantry 2.

In the exemplary embodiment of the invention, the filter body 22 performs a see-saw motion between −15° and +15° from its initial position shown in FIG. 2.

If the entire scan of the patient P is considered, via the reshaping or, respectively, adaptation of the intensity profile the filter also produces a savings of the dose of x-ray radiation applied to the patient P in the course of the scan.

In contrast to the described exemplary embodiment of the present invention, the filter body can also be designed differently in adaptation to the subject to be examined, i.e. can have a different shape. In particular, the blades can be of a different shape. Depending on the embodiment of the filter body, this can also rotate completely around the axle of the filter in order to respectively adapt the intensity profile of the x-ray radiation to the beam attenuation profile of the examination subject.

Furthermore, the filter material does not necessarily need to comprise aluminum and/or graphite. Rather, other suitable filter materials can also be used.

Moreover, the axle does not need to proceed through the middle of the filter 20 or of the filter body 22. The rotation axis can also be situated outside of the filter body 22, for example to the side or below the filter body 22. In order to be able to shape a desired intensity profile, the filter body is to be designed adapted to its rotation axis.

If necessary, the computed tomography apparatus 1 can have multiple different filters 20 that differ from one another with regard to their filter body and/or the rotation axis of the filter or of the filter body. The filter best suited to the examination is then always selected before an examination of an examination subject takes place with the computed tomography apparatus 1.

The x-ray device provided with the filter also does not necessarily need to be a computed tomography apparatus. The filter is also suitable for C-arm x-ray apparatuses and other x-ray apparatuses. In this context the beam of x-rays can also be pyramid-shaped or conical.

The filter according to the invention is moreover suitable not only to dynamically shape the intensity profile of the x-ray radiation emanating from an x-ray source. Rather, the intensity profile for an examination subject can also be optimized with the filter body in a fixed position.

Although modifications and changes may be suggested by those skilled in the art, it is the intention of the inventor to embody within the patent warranted hereon all changes and modifications as reasonably and properly come within the scope of his contribution to the art.

I claim as my invention:
1. An x-ray device comprising:
   an x-ray source that emits x-rays, having an intensity profile, in a beam that proceeds through a plane;
   said x-ray source being mounted to rotate around a rotation axis while emitting said x-rays in said beam, said rotation axis being perpendicular to said plane;
   a filter body comprised of material that attenuates said x-rays;

said filter body having a propeller shape and comprising two blades connected by an axle that proceeds between said two blades, said axle being oriented perpendicularly to said plane;

said axle being rotatable to move said two blades through different angles in said x-rays, said axle producing substantially no attenuation of said x-rays; and said two blades having respectively different cross-sections that cause each blade to differently attenuate said x-rays dependent on the angle at which each blade is placed by rotation of said axle, to shape said intensity profile of x-rays attenuated by said two blades.

2. The x-ray device of claim 1 wherein said two blades of said filter body are each configured to change radiography lengths of at least a portion of said x-rays dependent on rotation of said filter body by said axle.

3. The x-ray device of claim 1 wherein said x-ray source is configured to irradiate a patient having geometric dimensions that give said patient a patient attenuation profile, and wherein said two blades are rotatable by said axle to adapt said intensity profile of said x-rays to at least one of said geometric dimensions and said patient attenuation profile of said patient.

4. The x-ray device of claim 1 wherein a first of said two blades has a cross section that approximates a wave crest of a fluid wave, and a second of said two blades has a cross section that is approximately banana-shaped.

5. The x-ray device of claim 1 wherein said two blades of said filter body comprise filter material selected from the group consisting of aluminum and graphite.

6. An x-ray device as claimed in claim 1 wherein said beam is a beam selected from the group consisting of a pyramid-shaped beam, a conical beam, and a fan-shaped beam, said beam having an axis of symmetry in said plane, and wherein said filter body is mechanically mounted with respect to said x-ray source to cause radiography lengths of the x-rays in said beam, due to interaction of said x-rays of said beam with said filter body, to always be approximately symmetrical to said axis of symmetry, independently of rotation of said filter body.

7. An x-ray device as claimed in claim 1 comprising an x-ray detector on which x-rays emitted by said x-ray source are incident after attenuation by a patient, and a computed tomography apparatus that includes said x-ray source and said x-ray detector mounted on a gantry of said computed tomography apparatus together with said filter body, with the rotation of the x-ray source around said rotation axis causing said x-ray source to rotate around the patient.

8. An x-ray device as claimed in claim 7 wherein said patient has geometric dimensions and wherein the rotation of said x-ray source around said patient causes different geometrical dimensions of said patient to be irradiated by said x-rays thereby also causing a patient attenuation profile of said x-rays that irradiate the patient to change dependent on said rotation of said x-ray source, and wherein said two blades of said filter body are rotated by said axle to continuously or intermittently adapt said patient intensity profile of said x-rays to at least one of the different geometric dimensions and changing patient attenuation profile resulting from rotation of said x-ray source.

9. An x-ray device as claimed in claim 8 wherein said axle rotates said filter body with a see-saw motion.

* * * * *